United States Patent [19]

Shimada et al.

[11] Patent Number: 5,671,044
[45] Date of Patent: Sep. 23, 1997

[54] METHOD OF EXAMINING FILM QUALITY OF A MEMBRANAL MATERIAL AND AN APPARATUS THEREFOR

[75] Inventors: Yoshinori Shimada, Yamatokoriyama; Keiichi Tanaka, Taki-gun, both of Japan

[73] Assignee: Sharp Kabushiki Kaisha, Osaka, Japan

[21] Appl. No.: 571,101

[22] Filed: Dec. 12, 1995

[30] Foreign Application Priority Data

Dec. 12, 1994 [JP] Japan .................................. 6-307652

[51] Int. Cl.⁶ ............................................. G01N 21/00
[52] U.S. Cl. ........................ 356/237; 356/376; 356/382; 356/432
[58] Field of Search .................. 356/237, 276, 356/382, 432

[56] References Cited

U.S. PATENT DOCUMENTS 5,452,079  9/1995  Okugawa ........................... 356/237
5,528,359  6/1996  Taguchi ............................. 356/237

FOREIGN PATENT DOCUMENTS 5142524  6/1993  Japan .

*Primary Examiner*—Frank G. Font
*Assistant Examiner*—Reginald A. Ratliff

[57]  ABSTRACT

Polarized test light is radiated on the rear surface of a test film placed on a light-transmissive substrate, so that the quality of the film is detected by observing a color-irregularity pattern formed on the front surface of the test film. An apparatus of this detection includes: a light-transmissive substrate on which a test film is placed; a planar light source disposed on the rear side of the substrate; and a polarizing plate disposed between the planer light source and the light-transmissive substrate. The polarizing plate is preferably provided rotatable.

6 Claims, 3 Drawing Sheets

METHOD OF EXAMINING FILM QUALITY OF A MEMBRANAL MATERIAL AND AN APPARATUS THEREFOR

BACKGROUND OF THE INVENTION

(1) Field of the Invention

The present invention relates to a method of examining film quality of a membranal material such as an insulating film, semiconductor film or the like which is used to form a laminate structure for a liquid crystal device and the like. The present invention also relates to an apparatus of attaining the same method.

(2) Description of the Prior Art

Recently, active matrix drive type display devices have been widely used for liquid crystal television sets, word processors, computer terminal appliances and the like. This active matrix drive type device is composed of a great number of pixel electrodes arranged matrix-wise on an insulator substrate, each connected with a thin-film transistor element and is driven such that thin-film transistor elements are controlled separately to independently drive the pixel electrodes.

A typical liquid crystal display device of this kind is composed of insulator films and semiconductor films laminated. Therefore, if any of insulator films and semiconductor films are not formed uniformly, this ununiformity could cause display unevenness. Accordingly, there has been a strong demand on simple examining methods and apparatuses of examining membranal materials such as the insulator films, semiconductor films and the like.

FIG. 1 is a view schematically showing a principle of a prior art method of examining film quality. In this conventional method, a film 1 to be tested (to be referred to as a tested film 1 hereinbelow) was formed on a light-transmissive substrate 2 of a glass plate etc. Test light 4 emitted from a two-dimensional or planar light source 3 disposed under the light-transmissive substrate 2 was irradiated on the rear surface of the tested film 1. In this arrangement, an examiner observed the upper surface of the tested film 1 by naked eyes 5 and checked the brightness and color tones, so as to determine the film quality of the tested film 1.

In general, the tested film 1 made of an insulator film or semiconductor film is light-transmissive and if there is an irregular portion or there is some dissimilar quality in the film 1, the light having passed through the film 1 presents aniso-quality in brightness and/or color tone. Accordingly, this feature can be used to know irregularity of the film quality, so that the examiner visually observed the film to check it.

In accordance with this conventional method and apparatus of examining film quality, it is possible to make the unevenness stand out as long as the film contains noticeable variations in its quality. However, by this method, it is impossible for the examiner to check minute variations in the film quality. Particularly, if film thickness changes, the film presents irregularity in the brightness and color tones due to the variations of the film thickness. Therefore, this made it difficult for the checker to examine the film by comparison. Further, since the standard of selection for picking out the products, largely differs depending on examiner's experience, there was a problem that the individual difference would make the quality of products dissimilar or dispersed.

SUMMARY OF THE INVENTION

It is therefore an object of the present invention to provide a simplified and precision-improved method and apparatus of examining film quality of a membranal material, without requiring examiner's skillfulness and experience. The gist of the invention is as follows:

First, a method of examining film quality of a membranal material includes the steps of: radiating polarized test light created through a polarizing plate, on the rear surface of a light-transmissive substrate on which a tested membranal material is formed; and detecting film quality of the tested membranal material based on a color-irregularity pattern formed on the surface of the tested membranal material.

In the above configuration, it is effective that the polarizing plate is rotated relative to the light-transmissive substrate.

Next, an apparatus of examining film quality of a membranal material includes: a light-transmissive substrate with a tested membranal material to be formed on the front surface thereof; a planar light source disposed on the rear side of the light-transmissive substrate; and a polarizing plate disposed between the planar light source and the light-transmissive substrate.

In the above configuration, any of the following features are effective: the polarizing plate is rotatably provided between the planar source and the light-transmissive substrate; the apparatus further includes an adjusting mechanism for inclining a stage on which the light-transmissive substrate is placed, against the incident direction of the polarized test light; and the apparatus further includes a mechanism for rotating the light-transmissive substrate with the polarized plate fixed.

Thus, the examining method and the examining apparatus of the invention are thus configurated. Therefore, in accordance with the invention, when polarized test light is radiated on the rear surface of a tested film, optical distortions at interfaces between film layers or in affected zones can be emphasized and appear as color irregularity on the surface of the tested film. Further, as the polarized plate is rotated in a plane perpendicular to the incident direction of the test light, the color-irregularity pattern on the surface of the test film varies. As a result, it is possible for any examiner who does not have any skill to easily recognize minute variations of the film quality.

DESCRIPTION OF THE PREFERRED EMBODIMENTS

Figure 1:
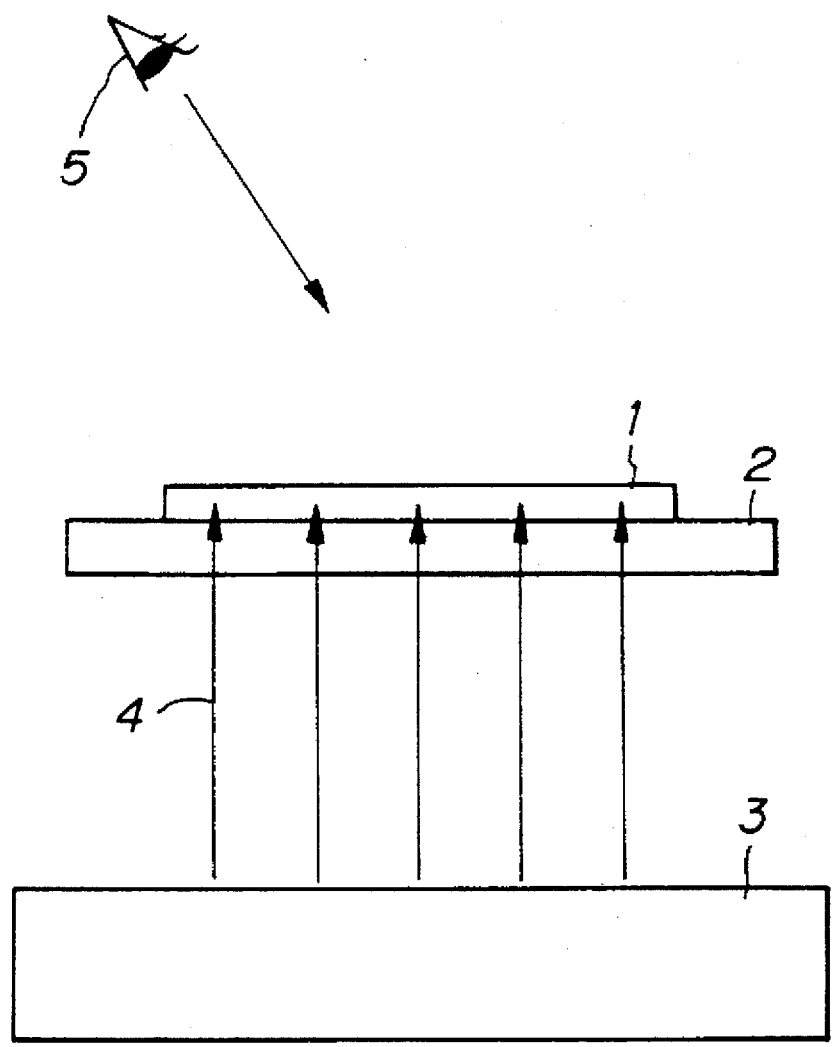
FIG. 1 is a view showing the principle of a conventional method of examining film quality.
Figure 2:
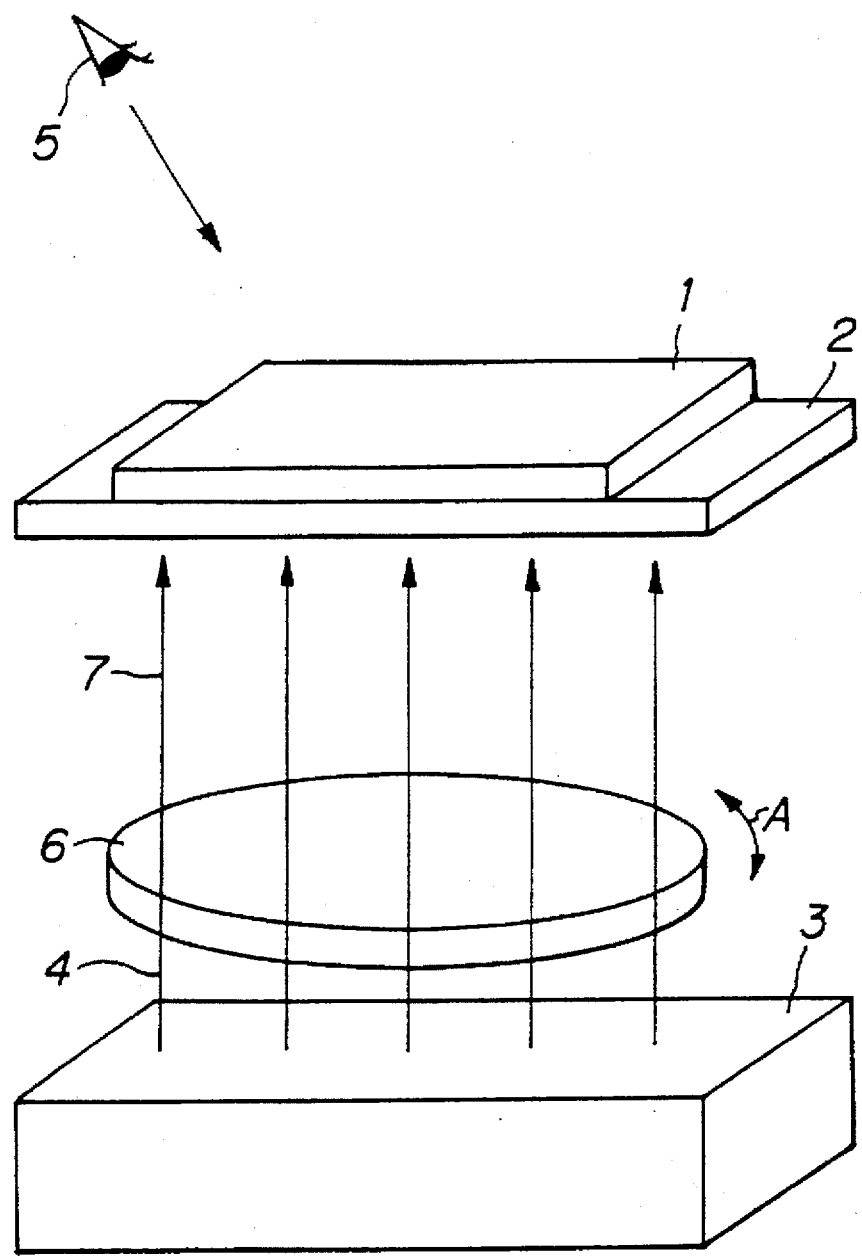
FIG. 2 is a schematic illustrative view for explaining the principle of a method of examining film quality of a membranal material in accordance with the invention.

FIG. 2 is a schematic illustrative view for explaining the principle of a method of examining film quality of a membranal material in accordance with the invention. In this figure, the same components with those in FIG. 1 are allotted with identical reference numerals. In this embodiment, a polarizing plate 6 is provided between a light-transmissive substrate 2 and a planar light source 3. Test light 4 emitted from the planar light source 3 is polarized by the polarizing plate 6 so that the light-transmissive substrate 2 is irradiated with polarized test light 7.

In this arrangement, a tested film 1 is formed on the light-transmissive substrate 2. The rear surface of the tested film 1 is irradiated with the polarized test light 7. The examiner observes the upper surface of the tested film 1 with naked eyes 5, so as to judge whether there is any color-irregularity pattern. If there is color irregularity, the portion is determined as to be an affected zone. If there is no unevenness in its color, the product is determined to come up to the standard.

During the test, if the polarizing plate 6 is rotated in directions of arrows A, the color-irregularity pattern in the affected zone varies as it is rotated. This feature makes it possible for an unskilled examiner to easily detect the irregularity even if the unevenness in the film quality is fine and minute. In this way, it is possible to provide an improved method of examining film quality without requiring skilled experience for the examiner.

Figure 3:
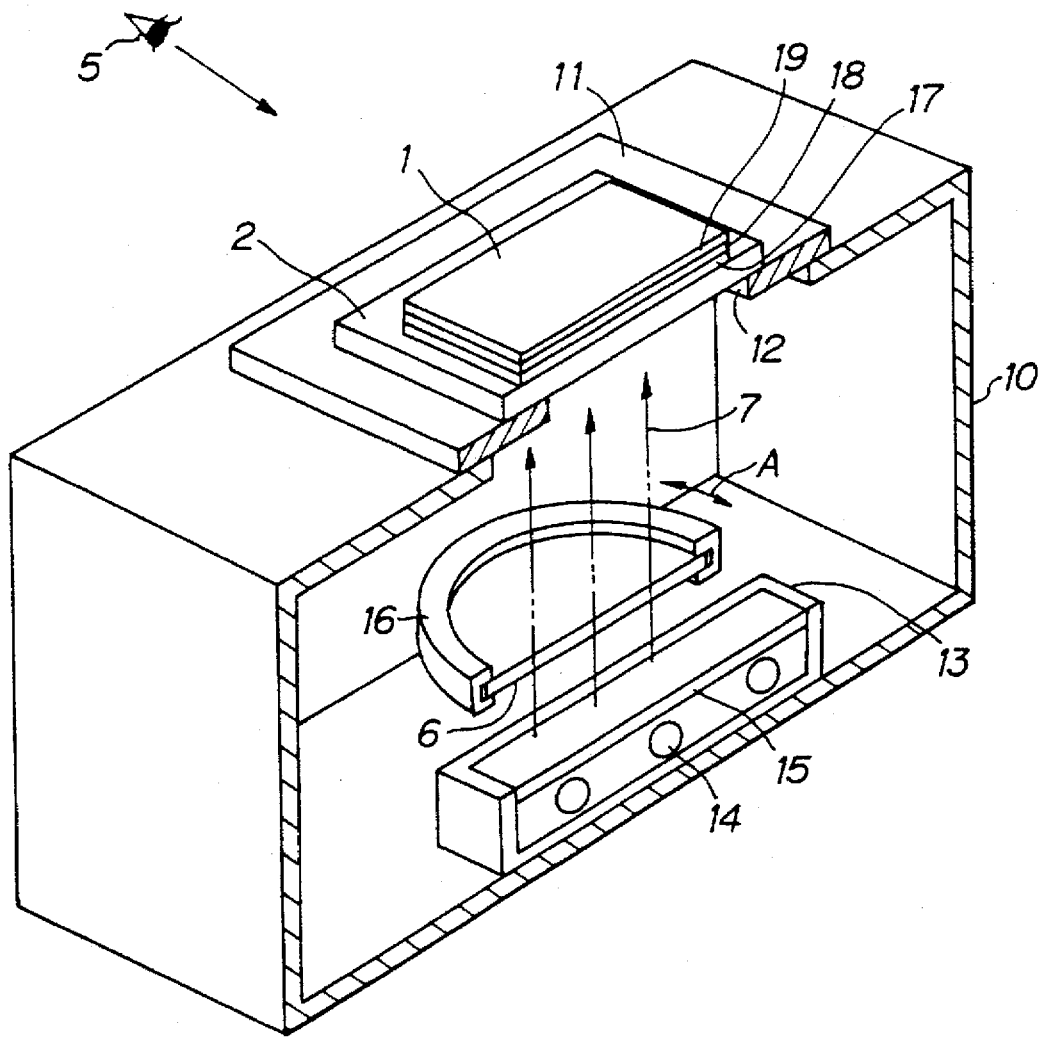
FIG. 3 is a partially cutaway, perspective view showing a vertical section of an apparatus of examining film quality in accordance with the invention.

FIG. 3 is a partially cutaway, perspective view showing a vertical section of an embodiment of an apparatus of examining film quality of a membranal material in accordance with the invention. This apparatus of examining film quality is housed by a frame casing 10. A stage 11 for setting a test piece is provided on the top of the frame casing 10. A lighting window 12 for allowing test light to pass therethrough is provided in the central part of the stage 11. A light-transmissive substrate 2 with a tested film 1 thereon is placed over the lighting window 12.

Provided on the bottom of the frame casing 10 is a planar light source 13. This planar light source 13 is composed of cold cathode fluorescent lamps 14 and a yellow band-pass filter 15 (of a wavelength of 500 nm) covering the lamps. A polarizing plate 6 is disposed between the planar light source 13 and the light-transmissive substrate 2. This polarizing plate 6 is supported by a rotary holder 16, which allows the polarizing plate 6 to rotate in directions of arrows A.

In the thus configurated apparatus of examining film quality, the light-transmissive substrate 2 having a tested film 1 formed thereon is set around the lighting window 12 on the stage 11 while polarized test light 7 is irradiated on the rear surface of the tested film 1. In this condition, the examiner examines the quality of the tested film 1 by visually observing its surface with naked eyes 5.

In this embodiment, a glass plate of 1.1 mm thick is used as the light-transmissive substrate 2. The tested film 1 is composed of insulator layers 17 and 19 consisting of silicon nitride and a semiconductor layer 18 consisting of amorphous silicon. As to the polarizing plate 6, the degree of polarization is 99.8%, the transmittance is 40%. The polarizing plate 6 is rotatably mounted to the rotary holder 16 so as to form light emitted from the planar light source 13 into plane-polarized test light 7 that is rotatable by 360°. The thus produced plane-polarized test light is made to irradiate on the rear surface of the light-transmissive substrate 2.

The polarized test light 7 is made incident on the rear side of the light-transmissive substrate 2 and to pass through the tested film 1. If there is any affected zone at the interface between the light-transmissive substrate 2 and the insulator layer 17 or the interface between the insulator layer 17 and the semiconductor layer 18 or on the surface of the tested film 1, the optical distortion in the affected layer is emphasized by the polarized test light 7 during the passage of the light, thereby presenting a color-irregularity pattern on the surface of the tested film 1. Since this color-irregularity pattern varies when the polarizing plate 6 is rotated in the plane perpendicular to the incident direction of the test light 7, it is possible for an examiner to easily detect affected areas even if they are minute, regardless of the skillfulness or experience of the examiner.

In the description of the above embodiment, a monochromatic light source created by the combination of the cold cathode fluorescent lamps 14 and the yellow band-pass filter 15 is used as an example of the planar light source 13. However, the invention is not limited to this configuration. That is, a different band-pass filter having another range of wavelengths can be used or plural band-pass filters can be mounted in order for the examiner to easily detect color unevenness. Alternatively, the apparatus can be configured so that a proper band-pass filter can be selected from the above plural band-pass filters, depending upon the type of the test target.

As the light-transmissive substrate 2, a dedicated substrate for test may be used or a substrate which is a part of a product to be tested may be used by itself. An adjusting mechanism may be provided for inclining the stage 11 having the light-transmissive substrate 2 placed thereon, against the incident rays of light. In such a configuration, the incident rays of the polarized test light 7 interfere with the multiply reflected polarized test light inside the tested film 1 so that interference fringes are formed on the surface of the tested film 1. The interference fringe pattern thus formed can be used as an indicator to detect minute variations of the film thickness. As an alternative configuration, a light-transmissive substrate 2 may be made rotatable in place of the polarizing plate 6.

In accordance with the invention, the polarized test light is irradiated on the rear surface of the laminate structure of the light-transmissive substrate and tested film, so that the optical distortion of the laminate structure is emphasized to form a color-irregularity pattern on the surface of the tested film. This configuration makes it is possible for an examiner to easily detect the quality of the film to be tested.

Particularly, since when the polarized plate is rotated relative to the light-transmissive substrate, the color-irregularity pattern on the surface of the tested film varies, it is possible for an examiner to easily detect minute variations of the film quality, even if the examiner is unskilled.

What is claimed is:

1. A method of examining film quality of a membranal material comprising the steps of:

radiating polarized test light created through a polarizing plate, on the rear surface of a light-transmissive substrate on which a tested membranal material is formed;

rotating said polarizing plate relative to said light transmissive substrates; and detecting film quality of said tested membranal material based on changes in a color-irregularity pattern formed on the surface of said tested membranal material during said rotating.

2. An apparatus for examining film quality of a membranal material comprising:

a light-transmissive substrate with a tested membranal material to be formed on the front surface thereof;

a planar light source disposed on the rear side of said light-transmissive substrate;

a polarizing plate disposed between said planar light source and said light-transmissive substrate; and means for rotating said polarizing plated said light transmissive substrate relative to one another.

3. The apparatus for examining film quality of a membranal material according to claim 2, further comprising an adjusting mechanism for inclining a stage on which said light-transmissive substrate is placed, against the incident direction of said polarized test light.

4. The apparatus for examining film quality of a membranal material according to claim 2, further comprising a mechanism for rotating said light-transmissive substrate with said polarized plate fixed.

5. The method according to claim 1, further comprising aligning said light transmissive substrate to receive said polarized test light orthogonally thereon.

6. The apparatus according to claim 3, further comprising means for aligning said light transmissive substrate to receive said polarized test light orthogonally thereon.

* * * * *